United States Patent [19]

Scallen et al.

[11] 4,169,944
[45] Oct. 2, 1979

[54] CHOLESTEROL BIOSYNTHESIS INHIBITORS

[75] Inventors: Terence J. Scallen; Cary J. Morrow, both of Albuquerque, N. Mex.

[73] Assignee: University Patents, Inc., Norwalk, Conn.

[21] Appl. No.: 834,324

[22] Filed: Sep. 19, 1977

[51] Int. Cl.$^2$ ............................................. C07H 17/00
[52] U.S. Cl. ........................................ 536/27; 536/28; 536/29; 424/180
[58] Field of Search ........... 536/27; 260/455 R, 535 P

[56] References Cited

U.S. PATENT DOCUMENTS

| | | | |
|---|---|---|---|
| 2,550,141 | 4/1951 | Doumani | 260/455 R |
| 3,036,093 | 5/1962 | Lynn | 260/455 R |
| 3,402,194 | 9/1968 | Schleppnik | 260/455 R |

OTHER PUBLICATIONS

Chem. Abstracts, 85, 1651e.
General Biochemistry, John Wiley & Sons, Inc., 1958, p. 510.
Chem. Abstracts, 85, 155390f.

*Primary Examiner*—Johnnie R. Brown
*Assistant Examiner*—Blondel Hazel
*Attorney, Agent, or Firm*—Mason, Kolehmainen, Rathburn & Wyss

[57] ABSTRACT

Cholesterol biosynthesis inhibitors are described which are derivatives of coenzyme A having the general formula

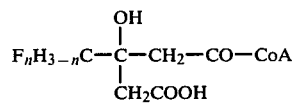

wherein n is 1 to 3, inclusive, and CoA is coenzyme A minus a hydrogen atom from a sulfhydryl substituent. They are produced by reacting coenzyme A with a fluorinated 3-hydroxy-3-methylglutaric anhydride of the general formula

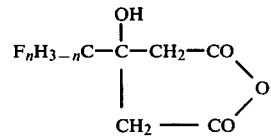

in dilute aqueous alkali.

3 Claims, No Drawings

CHOLESTEROL BIOSYNTHESIS INHIBITORS

This invention relates to fluorinated 3-hydroxy-3-methyl-glutaryl-coenzyme A and the production thereof.

BACKGROUND OF THE INVENTION

The major regulatory enzyme is hepatic cholesterol biosynthesis is 3-hydroxy-3-methylglutaryl-coenzyme A reductase (HMG-CoA reductase or EC 1.1.1.34) which catalyzes the reduction of 3-hydroxy-3-methyl-glutaryl-coenzyme A (HMG-CoA) to mevalonic acid. Inhibitors of HMG-CoA reductase inhibit or regulate the biosynthesis of cholesterol in mammals and are valuable agents in the prevention of adverse physiological effects induced by cholesterol.

OBJECTS OF THE INVENTION

It is an object of this invention to provide inhibitors of cholesterol biosynthesis. It is a further object to provide a method of production of such inhibitors. Another object is to provide a synthetic procedure for 3-hydroxy-3-trifluoromethyl-glutaryl-coenzyme A and similar products. An additional object is to provide fluorinated derivatives of 3-hydroxy-3-methyl-glutaryl-coenzyme A as inhibitors and regulators of cholesterol biosynthesis. These and other objects are apparent from and achieved in accordance with the following disclosure.

GENERAL DESCRIPTION OF THE INVENTION

We have discovered that derivatives of 3-hydroxy-3-methylglutaryl-coenzyme A which contain fluorine atoms on the 3-methyl group are effective inhibitors of 3-hydroxy-3-methylglutaryl-coenzyme A reductase. Particularly desirable as an inhibitor is 3-hydroxy-3-trifluoromethylglutaryl-coenzyme A, although similar products containing one or two fluorine atoms on the 3-methyl group are also effective inhibitors. These substances are useful as regulators of blood cholesterol levels in mammals.

The inhibitors of this invention have the general formula

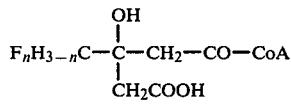

wherein n is an integer from 1 to 3, inclusive. The 3-hydroxy-3-fluoromethylglutaryl moiety is linked to coenzyme A through a sulfur atom, the latter occurring in the —SH group of coenzyme A.

Inhibitory activity of trifluoro-HMG-CoA has been observed at the following five levels of biological organization: (i) purified rat liver 3-hydroxy-3-methylglutaryl-coenzyme A (HMG-CoA) reductase, the major regulatory enzyme in cholesterol biosynthesis; (ii) crude soluble HMG-CoA reductase; (iii) rat liver microsomal HMG-CoA reductase; (iv) incorporation of [1-$^{14}$C] acetate into cholesterol (nonsaponifiable extract) in intact liver cells; and (v) liver microsomal HMG-CoA reductase from rats treated with trifluoro-HMG-CoA.

Trifluoro-HMG-CoA is produced as follows: 3-Hydroxy-3-trifluoromethylglutaric acid (Griot et al U.S. Pat. No. 3,671,583) is converted to 3-hydroxy-3-trifluoromethylglutaric anhydride by treatment with dicyclohexylcarbodiimide and the anhydride is reacted with coenzyme A in dilute alkaline solution at ice temperature. After the reaction has been completed, the pH of the solution is adjusted to 5.5 to 6.0 and frozen. The inhibitor can be stored frozen and used in the thawed solution. 3-Hydroxy-3-monofluoromethylglutaryl-coenzyme A and 3-hydroxy-3-difluoromethylglutaryl-coenzyme A can be prepared by the procedure described above. 3-Hydroxy-3-monofluoromethylglutaric acid and 3-hydroxy-3-difluoromethylglutaric acid are converted to 3-hydroxy-3-monofluoromethylglutaric anhydride and 3-hydroxy-3-difluoromethylglutaric anhydride, respectively, and the anhydrides reacted with coenzyme A in dilute alkaline solution. The inhibitors are stored and used in the same way.

DETAILED DESCRIPTION OF THE INVENTION

Table I shows the results of an experiment in which HMG-CoA reductase activity was assayed in a crude soluble extract of rat liver microsomes in the presence of varying concentrations of trifluoro-HMG-CoA. As can be seen in Table I, significant inhibition occurred at trifluoro-HMG-CoA concentrations of 0.1 and 1.0 mM.

| Trifluoro-HMG-CoA concentration (mM) | HMG-CoA reductase activity (nmol mevalonate formed/min/ml) | Inhibition % |
|---|---|---|
| 0.00 | 1.98 | 0 |
| 0.01 | 1.85 | 7 |
| 0.10 | 1.29 | 35 |
| 1.00 | 0.44 | 78 |

Crude soluble extract from rat liver microsomes was prepared as previously described (2). HMG-CoA reductase activity and incubation conditions were conducted as previously described (2,3).

The data in Table II show that trifluoro-HMG-CoA produces substantial inhibition of purified HMG-CoA reductase. At a trifluoro-HMG-CoA concentration of 1.1 mM, 73% inhibition was observed.

TABLE II

Inhibition of purified HMG-CoA reductase by 3-hydroxy-3-trifluoromethylglutaryl coenzyme A (trifluoro-HMG-CoA).

| Trifluoro-HMG-CoA concentration (mM) | HMG-CoA reductase specific activity (nmol mevalonate) formed/min/mg protein) | Inhibition % |
|---|---|---|
| 0.0 | 931.9 | 0 |
| 1.1 | 253.5 | 73 |

HMG-CoA reductase was purified from rat liver microsomes as previously described (2). HMG-CoA reductase activity assay and incubation conditions were conducted as previously described (2,3).

Table III summarizes the results of an experiment in which the kinetics of inhibition of rat liver microsomal HMG-CoA reductase by trifluoro-HMG-CoA were measured. The results show that trifluoro-HMG-CoA is a competitive inhibitor of the natural substrate HMG-CoA with $K_I$ for trifluoro-HMG-CoA equal to 54 $\mu$M.

TABLE III

Inhibition of rat liver microsomal HMG-CoA reductase activity by 3-hydroxy-3-trifluoromethylglutaryl coenzyme A (trifluoro-HMG-CoA). A summary of the kinetic data is shown.

$K_m$ for HMG-CoA = 34.5 μM
$K_m'$ for HMG-CoA in the presence of trifluoro-HMG-CoA = 417 μM
$K_I$ for trifluoro-HMG-CoA = 54 μM
Inhibition type for trifluoro-HMG-CoA is competitive The velocity of mevalonate formation was first measured in the absence of trifluoro-HMG-CoA, varying the concentration of the substrate [3-$^{14}$C]HMG-CoA. Then the same experiment was conducted in the presence of trifluoro-HMG-CoA (600 μM). The data were analyzed by means of an Eadie-Hofstee plot.

Table IV shows the results of an experiment in which the incorporation of [1-$^{14}$C] acetate into cholesterol (nonsaponifiable extract) was measured in intact liver cells with varying concentrations of trifluoro-HMG-CoA. As can be seen in the Table significant inhibition of cholesterol formation occurred with trifluoro-HMG-CoA concentrations as low as 0.01 mM. It was calculated from this experiment that 50% inhibition occurred at a trifluoro-HMG-CoA concentration of approximately 40 μM.

TABLE IV

Inhibition of the incorporation of [1−$^{14}$C] acetate into cholesterol (nonsaponifiable extract) in intact rat liver cells by 3-hydroxy-3-trifluoromethylglutaryl coenzyme A (trifluoro-HMG-CoA).

| Trifluoro-HMG-CoA concentration (mM) | Inhibition of the incorporation of [1−$^{14}$C] acetate into cholesterol (nonsaponifiable extract) % |
|---|---|
| 0.00 | 0 |
| 0.01 | 34 |
| 0.10 | 67 |
| 1.00 | 88 |

Duplicate samples contained 3.7 ml of hepatocyte suspension and 0.28 ml of saturated KHCO$_3$ (pH 5.7–5.9) which contained varying final concentrations (0, 0.01, 0.10 or 1.0 mM) of trifluoro-HMG-CoA. Preincubation was conducted for 60 minutes. 10 μCi of [1-$^{14}$C] sodium acetate, dissolved in Krebs Ringer bicarbonate buffer, was then added to each sample. Incubation was conducted for 120 minutes in a Dubnoff shaker. Saponification and extraction were conducted as previously described (4).

Table V shows the results of an experiment in which rats were treated with trifluoro-HMG-CoA (0.2 mg per injection) for 6 days. Control rats received an injection of the vehicle (KHCO$_3$ buffer) used for trifluoro-HMG-CoA injection. Liver microsomes were isolated from these animals, and HMG-CoA reductase activity was measured. The control group average HMG-CoA reductase specific activity was 1.25 nmol mevalonate formed/min/mg protein. The rats treated with trifluoro-HMG-CoA had an average HMG-CoA reductase specific activity of 0.63 nmol mevalonate formed/min/mg protein. This difference was statistically significant at the p=0.005 level. The control group and the trifluoro-HMG-CoA treated group were of the same age and sex, and the total body weights and liver weights were not significantly different in the two groups.

TABLE V

Liver microsomal HMG-CoA reductase activity in normal rats and in rats treated with 3-hydroxy-3-trifluoromethylglutaryl coenzyme A (trifluoro-HMG-CoA).

| | HMG-CoA reductase specific activity (nmol mevalonate formed/min/mg protein) | |
|---|---|---|
| | Normal rats | Trifluoro-HMG-CoA treated rats |
| | 1.02 | 0.59 |
| | 1.13 | 0.83 |
| | 1.83 | 0.58 |
| | 0.69 | 0.95 |
| | 1.41 | 0.40 |
| | 1.44 | 0.42 |
| Average | 1.25 | 0.63 |

Twelve male rats of identical age were used. Six rats served as the control group; these rats received an intraperitoneal injection of KHCO$_3$ buffer (0.2 ml) once per day (3:00 pm) for six days, except on the final day when additional injections were given at 10:00 pm and 6:00 am the following day. The drug-treated group of six rats received intraperitoneal injections of trifluoro-HMG-CoA (0.2 mg) in KHCO$_3$ buffer (0.2 ml) on the same schedule as described above for the control group. The data were further analyzed by the t statistic between the mean for each group.

The experimental data presented above demonstrate that trifluoro-HMG-CoA is an inhibitor of cholesterol biosynthesis. The relative potencies, as HMG-CoA reductase inhibitors, of trifluoro-HMG-CoA, trifluoro-HMG and trifluoro-HMG anhydride were investigated. It was found that at 1 mM final concentration trifluoro-HMG-CoA produced 78% inhibition of crude soluble HMG-CoA reductase (Table VI). Under similar circumstances 3-hydroxy-3-trifluoromethylglutaric acid (1 mM) produced 11% inhibition and 3-hydroxy-3-trifluoromethylglutaric anhydride produced 27% inhibition. Thus, trifluoro-HMG-CoA is a substantially more potent inhibitor than the free acid [3-hydroxy-3-trifluoromethylglutaric acid].

The inhibition of HMG-CoA reductase activity was measured in crude soluble extract from rat liver microsomes. The results are given in Table VI. Crude soluble extract from rat liver microsomes was prepared as previously described (2). HMG-CoA reductase activity and incubation conditions were conducted as previously described (2,3). The HMG-CoA reductase activity of the crude soluble extract in the absence of inhibitor was considered as 100% and activities measured in the presence of inhibitors were compared to this norm.

TABLE VI

| Inhibitor | Inhibitor Concentration (mM) | Inhibition of HMG-CoA reductase activity % |
|---|---|---|
| Trifluoro-HMG | 1 | 11 |
| Trifluoro-HMG-anhydride | 1 | 27 |
| Trifluoro-HMG-CoA | 1 | 78 |

The invention is further illustrated by the following examples.

EXAMPLE 1

Synthesis of 4-Hydroxy-4-Trifluoromethyl-1,6-Heptadiene

Allylmagnesium bromide was prepared from 140 g (1.16 mole) of allyl bromide, 35 g (1.44 mole) of magnesium and 640 ml of ether. The product was titrated and found to be 1.2 molar in allylmagnesium bromide. To a 230 ml (0.276 mole) aliquot of the reagent was added 17.4 g (0.122 mole) of ethyl trifluoroacetate in 60 ml of dry tetrahydrofuran at a drop rate of 2-3 drops/second. The reaction temperature was held near −40° during the addition. The reaction mixture was allowed to warm to room temperature and stirred overnight. It was heated at reflux for two hours, then stirred for an additional 24 hours. The reaction mixture was poured into 300 ml of ice and 20% sulfuric acid was added to bring the pH to about 1. The phases were separated and the aqueous phase extracted with 3×70 ml of ether. The combined organic phases were dried over magnesium sulfate, filtered and the solvent evaporated. The liquid product was distilled in vacuo to give 15.2 g (70%) of 4-hydroxy-4-trifluoromethyl-1,6-heptadiene, bp 54.5-58.5° C./30 torr.

nmr (CDCl$_3$): δ4.8-6.1 (characteristic multiplet, 6H, vinyl protons); δ2.5 (d, J =6, 5H) methylene and hydroxyl protons.

EXAMPLE 2

Synthesis of 3-Hydroxy-3-Trifluoromethylglutaric Acid

Into a solution of 9.3 g (0.052 mole) of 4-hydroxyl-4-trifluoromethyl-1,6-heptadiene in a mixture of 250 ml of dichloromethane and 15 ml of acetic acid was passed a stream of ozone in oxygen. After two hours, completion of the ozone addition was indicated by the characteristic blue color of excess ozone. The reaction mixture was allowed to warm to room temperature and the methylene chloride was evaporated and replaced with 300 ml of acetic acid. Finally, 60 ml of 30% hydrogen peroxide was added and the resulting mixture was refluxed overnight. The acetic acid was evaporated in vacuo. The residue was dissolved in ether and then toluene was added; the solvent mixture was evaporated in a rotary evaporator until crystals appeared. After cooling to room temperature the mixture was placed in the freezer to complete crystallization. The crystals were collected and the filtrate further evaporated until crystallization began again. Three repetitions of the technique provided a total of 8.75 g (78%) of 3-hydroxy-3-trifluoromethylglutaric acid. The product had a mp of 102°-105° C.

EXAMPLE 3

3-Hydroxy-3-Trifluoromethylglutaric Anhydride

A solution of 1.30 g (0.0060 mole) of 3-hydroxy-3-trifluoromethylglutaric acid in 36 ml of dry acetone was prepared and cooled to −42° C. To it was added a solution of 1.24 g (0.0060 mole) of dicyclohexylcarbodiimide in 36 ml of dry acetone and the resulting mixture was stirred for 3 hours. The mixture was then filtered and allowed to warm to room temperature. Further precipitate appeared and was filtered off. The acetone was then evaporated. The pale orange residue was taken up in hot benzene and allowed to crystallize at 4° C. for 48 hours. The needle-like crystals of 3-hydroxy-3-trifluoromethylgulatric anhydride were filtered off and dried in vacuo mp 122°-125° C. The yield was 0.89 g, 75%.

EXAMPLE 4

3-Hydroxy-3-Trifluoromethylglutaryl-Coenzyme A (Trifluoro-HMG-CoA)

Coenzyme A (46.5 mg) was dissolved in distilled water (2 ml) at 0° C. through which nitrogen was being bubbled. The pH was adjusted to approximately 7.5 with 1 N KOH, then 0.6 ml of saturated KHCO$_3$ was added. To this solution was added 3-hydroxy-3-trifluoromethylglutaric anhydride (9.6 mg). The addition was performed slowly with intermittent stirring. The reaction was allowed to proceed at room temperature for 20 to 60 min. The disappearance of free SH groups was followed by the nitroprusside test. When free SH groups were no longer detected, the solution was adjusted to pH 5.6 with 2 M HCl. The solution, containing 3-hydroxy-3-trifluoromethylglutaryl coenzyme A (trifluoro-HMG-CoA), was then frozen and stored at −20° C.

We claim:

1. Fluorinated 3-hydroxy-3-methylglutaryl-coenzyme A, wherein the fluorine is attached to the 3-methyl radical.

2. A compound of the formula

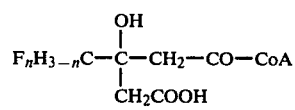

wherein CoA represents a coenzyme A residue and n is an integer from 1 to 3, inclusive.

3. A compound as defined by claim 2 wherein n is 3.